United States Patent [19]

Pak

[11] Patent Number: 4,772,467
[45] Date of Patent: Sep. 20, 1988

[54] OSTEOPOROSIS INHIBITION BY DIETARY CALCIUM SUPPLEMENTATION

[75] Inventor: Charles Y. C. Pak, Dallas, Tex.

[73] Assignee: Board of Regents, U T Systems, Austin, Tex.

[21] Appl. No.: 807,530

[22] Filed: Dec. 11, 1985

Related U.S. Application Data

[63] Continuation-in-part of Ser. No. 703,196, Feb. 19, 1985, abandoned.

[51] Int. Cl.$^4$ ..................... A61K 33/00; A61K 33/06
[52] U.S. Cl. .................................. 424/127; 424/154; 514/891
[58] Field of Search ................. 424/127, 154; 514/891

[56] References Cited

U.S. PATENT DOCUMENTS

| | | | |
|---|---|---|---|
| 3,105,792 | 10/1963 | White | 424/44 |
| 3,653,914 | 4/1972 | Schmidt | 99/78 |
| 4,107,346 | 8/1978 | Kravitz | 426/648 |
| 4,185,093 | 1/1980 | Carnes et al. | 424/153 |
| 4,214,996 | 7/1980 | Buddemmeyer et al. | 426/74 |
| 4,289,750 | 9/1981 | Kopp et al. | 424/33 |
| 4,405,596 | 9/1983 | Helbig et al. | 424/33 |
| 4,551,342 | 11/1985 | Natel et al. | 426/648 |
| 4,614,648 | 9/1986 | Bru | 424/44 |

FOREIGN PATENT DOCUMENTS

| | | |
|---|---|---|
| 0075429 | 9/1982 | European Pat. Off. |
| 761525 | 5/1951 | Fed. Rep. of Germany |
| 3014503 | 4/1980 | Fed. Rep. of Germany |
| 4384 M | 4/1966 | France |
| 7100516 | 3/1969 | Japan |
| 193065 | 1/1938 | Switzerland |
| 597936 | 11/1944 | United Kingdom |

OTHER PUBLICATIONS

Rubin Newspaper Clipping, (Austin American Statesman, 11/15/85).
Harvey et al., (J. Clin. Endocrin. Met., 61:1233, (1985)).
Nicar and Pack, (J. Clin. Endocrin. Met., 61:391, (1985).
Bo-Linn et al., (J. Clin. Invest., 73:640, (1984)).
Packett, et al., (1968), *J. Animal Science*, 27:1716–1721.
Butz and Dulce, Urolithiasis Clinical and Basic Research, (1980), Robertson et al. eds., Plenum Press, London, pp. 881–884.
Baruch et al., Med. Clin. N. Amer., (1975), 59:569–582.
Packett et al., (date not available), "Mineral Studies in Ovine Phosphatic Urolithiasis", pp. 1716–1720.
WO85/05552 International Publication, Dec. 19, 1985. PCT International Search Report.
Hunt and Johnson, (Digestive Dis. and Sci., 28:417, (1983)).
Leskovar et al., (Urol. Int., 36:325, (1981)).
Rudman et al., (N. Eng. J. Med., 303:657, (1980)).
Federal Register, (Mar. 16, 1979).
Unlisted Drugs, (1976), Reference C.
News Release from Proctor and Gamble.
Peacock et al., (Brit. Med. J., Jun., p. 729, (1968)).
Clarkson et al., (Clin. Sci., 30:425, (1966)).
McDonald et al., (Clin. Sci., 26:27, (1964)).
Niepmann, (Klin. Wochschr., 39:1064–1071, (1961)).
Rote Liste, (1961).
Jungmann et al., (Medizinische Klinik, (1934)).
Bonick, (1986), (Letter to Newsweek, 2/17/86).
Kolata, (Science, 233:519, (1986)).
Bishop article from the Wall Street Journal, (1986).
Abstract by Christiansen et al., (J. Bone Min. Res., 1, (1986)).
Abstract by Matkovit et al., (J. Bone Min. Res., 1, (1986)).
Abstract by Rigges et al., (J. Bone Min. Res., 1, (1986)).
Kotulak article, (Austin American Statesman, 3/30/86).
Brody, (N.Y. Times, 12/17/85).
Pekkanen, (Reader's Digest, 11/85).
Edelstein Article in Ladies Home Journal, (1985).
Sakhaee et al., (J. Clin. Endocrin. Met., 61:368, (1985)).
Consensus Development Conference Statement from the National Institute of Health, (1984).
Skilman, (Consultant, 2/84).
Kurtz et al., (Science, 222:1139, (1984)).
Ackley et al., (Am. J. Clin. Nutr., 38:457, (1983)).
Belizan, (J. Am. Med. Ass'n, 249:1161, (1983), #1)).
Belizan et al., (Am. J. Obstet. Gynecol., 146:175, (1983, #2)).
Nordenvall et al., (Eur. Urol., 9:35, (1983)).
McCarron et al., (Science, 217:267, (1982)).
McCarron, (1982), (N. Eng. J. of Med., 307:226).
Riggs et al., (New Eng. J. Med., 306:446, (1982)).
Strauss et al., (Am. J. Med., 72:17, (1982)).
Butz and Rost, (5th Symp. on Exptl. Urol., p. 243, (1980)).
Hartung et al., (5th Symp. on Exptl. Urol., p. 243, (1980)).
Nordin et al., (Brit. Med. J., p. 451, (1980)).
Barilla et al., (Am. J. Med., 64:579, (1978)).
Federal Register, (3/16/79).
Heaney et al., (J. Lab. Clin. Med., 92:953, (1978)).
Pak, (Calcium Nephrolithiasis, Plenum, N.Y., p. 5, (1978)).
Recker et al., (Ann. Int. Med., 87:649, (1977)).
Pak, (Urolithiasis Res., Plenum, N.Y. p. 213, (1976)).
Pak et al., (J. Clin. Invest., 54:387, (1974, #1)).
Pak et al., (N. Eng. J. Med., 290:175, (1974, #2)).
Chapter by Forbes and Demsey.
Pogainis and Shaw, (1957), (Proc. S. D. Acad. Sci., XXXVI, p. 56).
Chatterjee and Dhar (J. Physical Chemistry, 28:1009–1028, 1924).
International Search Report by the European Patent Office.
Dialog Search of the Patent and Scientific Literature.

*Primary Examiner*—John Rollins
*Attorney, Agent, or Firm*—Arnold, White & Durkee

[57] ABSTRACT

A process for dietary calcium supplementation. Oral dosage of a composition comprising calcium citrate is utilized to provide an efficiently absorbable chemical form of calcium, while raising urinary level of citrate. Because of improved absorption of calcium, osteoporosis development is precluded. Since citrate retards precipitation of stone-forming calcium stones, the risk of calcium nephrolithiasis (resulting from calcium supplementation) is reduced.

14 Claims, No Drawings

OSTEOPOROSIS INHIBITION BY DIETARY CALCIUM SUPPLEMENTATION

Research leading to development of the present invention was supported in part by grants P01-AM20543 and R01-AM-6061 from the National Institutes of Health, Department of Health and Human Services, United States of America.

CROSS-REFERENCE TO RELATED APPLICATIONS

This application is a continuation-in-part of co-pending application Ser. No. 703,196 filed Feb. 19, 1985, now abandoned.

BACKGROUND OF THE INVENTION

The mineral calcium is an important human dietary component. Calcium is required for adequate bone formation and maintenance, as well as for diverse metabolic functions. These diverse metabolic functions of calcium are incompletely understood but likely to involve, at least in part, the alteration and functional control of proteins such as enzymes, and of hormones that regulate bone metabolism.

An assurance of adequate dietary calcium intake is thus important for normal development, metabolism and maintenance. Dietary calcium intake alone however is insufficient to assure that adequate calcium levels are available for required body functions. Dietary calcium must be absorbed from the digestive tract before it may be utilized. The efficiency of calcium absorption is determined by several factors, including the physiological status of the patient and the particular chemical form of ingested calcium. However, a part of the absorbed calcium is eliminated in urine, which poses a problem for certain subjects who are prone to the formation of calcium-containing kidney stones (calcium nephrolithiasis).

Thus, the amount of calcium intake and efficiency of calcium absorption could influence two clinical conditions, osteoporosis and calcium nephrolithiasis.

A condition of particular relevance to calcium dietary requirement is osteoporosis. Osteoporosis, a condition characterized by decreases in bone mass, renders bones more fragile and susceptible to fracture. The increasingly older population of this country, since osteoporosis is usually an age-related phenomenon, further accentuates the significance of this condition. Postmenopausal women are generally agreed to be most susceptible to osteoporosis. These women have an impaired production of active vitamin D compound which normally stimulates calcium absorption. Because of this disturbed physiological status, they cannot absorb calcium efficiently from intestines, resulting in "negative calcium balance" (net loss of calcium from bone). Thus, they require an increased calcium intake to maintain a zero calcium balance and prevent calcium loss from bone (Heaney et al., J. Lab. Clin. Med., 1978, Vol. 92, No. 6, pp. 953-963). The NIH Concensus Development Conference on Osteoporosis (April 2-4, 1984) concluded that "an increase in calcium intake to 1,000 to 1,500 mg a day would reduce the incidence of osteoporosis in postmenopausal women". The Conference report also recommended calcium tablets "for those unable to take 1,000 to 1,500 mg calcium by diet". Increased calcium intake for elderly men was also recommended since their actual calcium intake may be less than that required to prevent negative calcium balance.

Because of frequent aversion to milk in elderly persons, various calcium supplements have been used to increase calcium intake. However, no distinction between calcium supplements was recognized (Consensus Development Conference on Osteoporosis). Skillman concluded "most salts of calcium are acceptable as calcium supplements" (Skillman, T. G., Osteoporosis, Consultant, Feb. 1984, pp. 153-165).

Studies of the present applicant suggest that calcium bioavailability, or the amount of calcium available for intestinal absorption, may vary among different calcium preparations (Nicar and Pak (1985) J. Clin. Endocrin. & Metab. V. 61, pp. 391-393). These variations result from differing properties such as the low aqueous solubility of some salts (calcium carbonate and calcium phosphate) and the ability of some anionic components (such as citrate) to form soluble complexes with calcium. The aqueous solubility of many calcium salts decreases as pH increases. In the normally acid environment of gastric juice, most calcium salts dissolve and become bioavailable except at very high dosages. However, when gastric acidity is abnormally low resulting in a high pH (as in achlorhydria or in some elderly persons who have defective acid production), calcium bioavailability from calcium carbonate and calcium phosphate may be low because of their incomplete gastric dissolution. When calcium salts of lactate, citrate and carbonate are given, the anions released may tend to neutralize the gastric juice and impair further solubility of calcium salts. Calcium absorbability may also depend on the type and extent of soluble complexation of calcium. The calcium complex (such as calcium citrate) itself may be absorbable.

Thus, in postmenopausal women and elderly men with impaired efficiency of intestinal calcium absorption, the provision of calcium supplementation with a high bioavailability due to particular chemical form should facilitate correction of physiologically abnormal calcium absorption, thus preventing negative calcium balance and retarding osteoporosis development.

In certain individuals however, dietary calcium supplementation may increase urinary calcium and lead to formation of calcium-containing kidney stones (nephrolithiasis).

Kidney stone formation may result from a number of conditions, one of which is the presence of undue amounts of calcium in urine. Pak et al (N. Engl. J. Med. (1974) Vol. 290 pp. 175 to 180) have shown that urinary calcium levels and renal calcium stone formation are decreased when patients with a history of recurrent calcium nephrolithiasis are fed on low calcium diets and treated orally with cellulose phosphate. Pak (Urolithiasis Research (1976) ed. by H. Fleisch et al., Phenum Pub. Co., N.Y., N.Y. pp. 213-224) demonstrated that when patients with absorptive hypercalciuria are fed calcium gluconate, they exhibited increased urinary calcium, leading to an increased activity product ratio, a measure of the degree of urinary calcium oxalate saturation. Thus, calcium supplementation made them more prone to form kidney stones, since their urine became more supersaturated with respect to a common stone salt (calcium oxalate).

The risk of calcium nephrolithiasis in many postmenopausal women and in elderly men is probably small. Because they have physiologically impaired ability to absorb calcium, their urinary calcium may not increase sufficiently to cause calcium stone formation following calcium supplementation. However, some of these persons may have high urinary calcium to begin with or have relatively normal calcium absorption (Sakhaee, K. J. Clin. Endo. Metab. Vol. 61, 1985, pp. 368-373). In such persons, calcium supplementation may cause kidney stones. Early postmenopausal women or pre-menopausal women with adequate calcium absorption may be similarly at risk. This danger was recognized by the Consensus Development Conference on Osteoporosis which warned that excessive calcium intake "could cause urinary tract stones in susceptible people".

Supplementation of the diet with calcium appears to be an important step in the prevention of osteoporosis in postmenopausal women and elderly men who have physiologically insufficient calcium absorption from intestines. However, such calcium supplementation may cause the undesirable side effect of calcium-containing kidney stones, especially in persons with relatively normal intestinal calcium absorption such as in pre-menopausal or early postmenopausal women.

An optimum calcium supplement should exhibit superior calcium bioavailability in order to best avert negative calcium balance, and should also reduce the risk for kidney stone formation. Thus, a method of providing efficiently absorbed calcium while precluding calcium nephrolithiasis is needed.

SUMMARY OF THE INVENTION

Dietary calcium supplementation providing efficient calcium bioavailability with reduced risk for calcium kidney stone formation is accomplished by daily supplementing an individual's diet with calcium citrate comprising about 0.5 gm to about 2.0 gm calcium. Calcium is more efficiently absorbed with calcium citrate than with other available preparations. Moreover, such supplementation with calcium citrate raises urinary citrate, which retards formation of calcium stones.

DETAILED DESCRIPTION OF THE PREFERRED EMBODIMENTS

The present invention comprises a process for dietary calcium supplementation, using a form of calcium which is efficiently absorbed from the intestinal tract. This form of calcium also raises urinary citrate levels and reduces the possibility of calcium-based kidney stone formation caused by calcium supplementation. Such calcium supplementation is particularly desirable for preventing or halting osteoporotic development.

A preferred form of calcium as well as citrate utilized in the process of the present invention consists essentially of calcium citrate, illustrated by the formula:

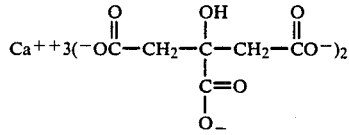

or the hydrate thereof. It is recognized that there are many methods of presenting a mixture of calcium salts and citrate salts which would be a substantial equivalent of gastrointestinally administered calcium citrate.

A pharmaceutically acceptable composition according to the present invention may be, for example, a formulation comprising calcium citrate, pregelatinized starch, magnesium stearate and carboxymethyl cellulose. The term "pharmaceutically acceptable" as used herein is defined to indicate a general non-toxicity and lack of irritative intestinal effects commensurate with a favorable benefit/risk ratio. A generally effective amount of the calcium citrate composition of the present invention suitable for daily administration comprises from about 0.5 gm to about 2 gm elemental calcium.

Normal subjects were given equivalent amounts of calcium as either calcium citrate or calcium carbonate and their extent of calcium absorption measured. Calcium was found to be more efficiently absorbed with calcium citrate, using two separate methods for measuring calcium absorption (Examples 1 and 2). Taking greater amounts of calcium carbonate did not substantially improve calcium absorption (Example 3). Similarly, postmenopausal women absorbed calcium more efficiently from calcium citrate than from calcium carbonate. Calcium absorption was also greater from calcium citrate than from other available calcium salts (calcium phosphate, calcium lactate, calcium gluconate) (Example 4).

Because it assures optimal calcium absorption, dietary calcium supplementation by oral administration of calcium citrate is a desirable method of precluding bone loss and osteoporosis.

Particular types of individuals are likely to optimally benefit from the dietary calcium supplementation according to methods of the present invention. These particular individuals include, for example, those at risk for osteoporosis. Generally the aging population, particularly those often regarded as aged, or well beyond the age of retirement, are apt to incur at least a degree of osteoporosis, particularly if their calcium intake is inadequate. Postmenopausal women, particularly at risk for osteoporosis, should be most greatly benefited as subjects of dietary calcium supplementation by the process of the present invention. In cases where a degree of osteoporosis has already occurred in a subject, dietary calcium supplementation according to the present invention should at least help prevent further osteoporotic development. Women approaching an age where menopause is likely to occur could begin dietary calcium supplementation by the process of the present invention to help avert any development of osteoporosis. Women subject to hysterectomies are also likely to benefit in analogous manner to calcium supplementation by the process of the present invention.

Many of the subjects previously mentioned may have low efficiency of calcium absorption due to a disturbed physiological status. Thus, they would be particular beneficiaries of calcium citrate supplements which provide improved absorbability of calcium due to its particular chemical form.

There is some evidence that calcium supplementation with calcium carbonate may not be completely effective in preventing osteoporosis. Recker et al. (Annals of Int. Med., 1977, Vol. 87, No. 6, pp. 649-655) and Nordin et al. (Brit. Med. J., 1980, Vol. 280, pp. 451-454) demonstrated that further bone losses in osteoporotic postmenopausal women may be retarded but not completely halted by calcium carbonate supplementation. Riggs et al. (N. Eng. J. Med., 1982, Vol. 306, pp. 446-450) showed that calcium carbonate supplementation reduced the rate of spinal fractures but did not eliminate it. Genant et al. found that spinal bone density continued to decline following calcium carbonate supplementation in postmenopausal women, though at a reduced rate (Copenhagen Intl. Symp. on Osteoporosis, 1984, Denmark: Aalborg Stiftsbogtrykkeri, pp. 65–72).

The incomplete effect of calcium carbonate in halting osteoporosis development could be due to inefficient calcium absorbability owing to its chemical form. There is some evidence that calcium citrate is more effective in halting bone loss (Example 5) due to its particular chemical form and improved calcium absorbability.

In one aspect, the present invention presents a composition and process for combatting development of osteoporosis. Individuals, such as those described above, who are susceptible to development of osteoporosis are identified. Those individuals already having a degree of osteoporosis are, or course, susceptible to further osteoporotic development. A composition comprising calcium in a chemical form adapted to provide efficiently gastrointestinally absorbable calcium ions is then provided. The individuals are then administered an effective amount of the composition on a continuing basis, preferably on a daily basis. This procedure is also adapted for dietary calcium supplementation of any individuals where dietary calcium supplementation is desired.

Calcium citrate supplementation should also be useful in halting osteoporosis development in persons who have physiologically adequate calcium absorption but whose normal dietary calcium intake is low. Such persons might be some postmenopausal women and premenopausal or early postmenpausal women. Because they have physiologically normal calcium absorption, they may develop hypercalciuria when they take calcium supplements, leaving them at risk to form calcium kidney stones. These subjects may particularly benefit from dietary calcium supplementation by the process of the present invention. The concomitant intestinal absorption of citrate and calcium provided by the process of the present invention succeeds in calcium supplementation while maintaining urinary conditions less favorable from calcium stone formation in the kidneys, although it may not altogether preclude the possibility of stone formation.

In earlier studies described in the Detailed Description of the Preferred Embodiment of co-pending U.S. patent application No. 741,745, incorporated by reference herein, by the same inventor and assigned to the same entity as the present application, the effectiveness of potassium citrate for treatment of calcium nephrolithiasis was described. Briefly, it was therein described that dietary potassium citrate treatment effectively raised urinary pH and citrate, and lowered urinary calcium oxalate saturation, while analogous sodium citrate treatment was found to increase urinary calcium oxalate saturation.

It has been found that calcium citrate dietary administration raises urinary pH, calcium content and citrate content while lowering ammonium content (Example 6). When equivalent levels of calcium carbonate were administered, urinary calcium content similarly increased but the rise in urinary citrate seen with calcium citrate administration did not occur. The rises in urinary citrate are important because it provides protection against the induction of calcium nephrolithiasis. Thus, because of this protective action, the stone-producing tendency of calcium supplements (from an increase in urinary calcium) is reduced when calcium citrate is the supplement.

Because it assures optimal calcium absorption while reducing the risk of nephrolithiasis, dietary calcium supplementation by oral administration of a composition consisting essentially of calcium citrate is a desirable method of precluding osteoporosis and bone loss, and of supplying adequate calcium for alleviation of any condition responsive thereto.

Precluded from calcium citrate supplementation are subjects with hypercalcemia or hypercalciuria especially when due to physiologically efficient calcium absorption. Some patients with existing calcium nephrolithiasis may have worsening of kidney stone formation since the rise in urinary citrate from calcium citrate supplementation sometimes may not be enough to overcome the stone-forming effect of the rise in urinary calcium.

The following examples are included to further describe preferred embodiments of the present invention and are not intended to limit the invention unless specifically indicated herein.

EXAMPLE 1

Calcium Absorption From Calcium Carbonate and Calcium Citrate

Four subjects were fed a control diet containing 400 mg calcium, 800 mg phosphorus and 100 millequivalents sodium/day. These subjects were then given either calcium carbonate or calcium citrate (10 millequivalents). The amount of calcium absorbed by the subjects on either supplementation was measured using isotopic techniques. It was found that calcium was more efficiently absorbed from the calcium citrate supplement than from the calcium carbonate supplement. All four subjects showed more efficient calcium absorption when supplemented with calcium citrate, the mean calcium absorption being 16.2% greater with calcium citrate than with calcium carbonate.

EXAMPLE 2

Calcium Bioavailability From Calcium Carbonate and Calcium Citrate

A recent study by the present applicant compared the calcium bioavailability from calcium citrate with that of calcium carbonate (Nicar and Pak, J. Clin. Endo. Metab., 1985, Vol. 61, pp. 391–393). Fourteen normal subjects (age 22–37) orally took 1000 mg of calcium as calcium citrate or calcium carbonate. The amount of calcium absorbed was estimated from the rise in urinary calcium. The rise in urinary calcium was significantly higher following oral administration of calcium citrate than of calcium carbonate, whether it was expressed as the total amount or as increments from basal (fasting) excretion. The mean change between two calcium phases ranged from 20% for total calcium excreted post-load, 52% for increment in urinary calcium over 4 hours post-load, to 66% for the increment in calcium excretion during the second half of post-load (Table 1). The greater rise in urinary calcium following calcium citrate load represents absorbability of calcium and reflects higher solubility of calcium citrate and availability of calcium.

TABLE 1

| INTESTINAL Ca ABSORPTION FROM CALCIUM CARBONATE AND CALCIUM CITRATE | | |
|---|---|---|
| | Calcium Carbonate Phase | Calcium Citrate Phase |
| Urinary Ca, 2-hr fast mg/dl GF | 0.064 ± 0.025 | 0.060 ± 0.025 |

TABLE 1-continued

INTESTINAL Ca ABSORPTION FROM CALCIUM CARBONATE AND CALCIUM CITRATE

|   | | Calcium Carbonate Phase | Calcium Citrate Phase |
|---|---|---|---|
| (a) | Urinary Ca, 4-hr post-load mg/mg Cr | 0.122 ± 0.067 | 0.147 ± 0.088* |
| (b) | Δ Urinary Ca, second half post-load, mg/dl GF | 0.064 ± 0.045 | 0.106 ± 0.087* |
| (c) | Δ Urinary Ca, first half post-load, mg/dl GF | 0.013 ± 0.036 | 0.025 ± 0.037 |
| (d) | Δ Urinary Ca, 4-hr post-load, mg/mg Cr | 0.048 ± 0.041 | 0.073 ± 0.058* |
| Serum Ca, mg/dl | | | |
| Fast | | 9.5 ± 0.4 | 9.5 ± 0.5 |
| Post-load | | 10.0 ± 0.4 | 10.2 ± 0.5 |

Values are presented as mean ± SD. Significant difference between two calcium phases is shown by: * for $p < 0.05$. Cr = creatinine, Δ = increment.

EXAMPLE 3

Calcium Absorption From Calcium Carbonate and Calcium Citrate

In 10 normal subjects, calcium absorption was measured from different amounts of ingested calcium (0.5 gm, 1.0 gm, 2.0 gm) as calcium citrate or calcium carbonate. At each level of calcium, calcium absorbed was greater from calcium citrate (at 0.5 gm calcium load, 0.102 mg/dl GF vs 0.040; at 1.0 gm calcium load, 0.107 vs 0.049; and at 2.0 gm calcium load, 0.113 vs. 0.056). Taking more calcium did not substantially improve calcium absorption. When 2 gm of calcium as calcium carbonate was given, the amount of calcium absorbed was less that that obtained from 0.5 gm of calcium as calcium citrate.

EXAMPLE 4

Calcium Absorption by Postmenopausal Women From Various Calcium Salts

In 4 postmenopausal women, calcium absorption was measured from 1 gm calcium orally given as different calcium salts. The magnitude of calcium absorption is indicated by the following series of salts: calcium citrate > calcium gluconate > calcium lactate > calcium phosphate > calcium carbonate.

EXAMPLE 5

Bone Density Of Postmenopausal Women As Function Of Calcium Supplementation

In 5 postmenopausal women, bone density of lumbar spines (L2-L4) was measured by dual photon absorptiometry. After 12 months of calcium citrate supplementation (800 mg calcium/day in divided doses), bone density did not change significantly but showed an average net change of +0.7%. This lack of change or slight improvement contrasts with the study of Genant et al. who found a decline in lumbar spinal density of 6.5% after 1 year of treatment with calcium carbonate (1 gm calcium/day). (Copenhagen Intl. Symp. on Osteoporosis, 1984, Denmark: Aalborg Stiftsbogtrykkeri, pp. 65-72).

EXAMPLE 6

Urinary Chemistry And Calcium Supplementation

A recent study indicated that calcium citrate supplementation is attendant with a lower risk of stone formation than that seen with calcium carbonate supplementation (Harvey, Zobitz and Pak, 1985, J. Clin. Endoc. Metab., Vol. 61, pp. 1223-1225). Calcium citrate supplementation (800 mg calcium/day in 4 divided doses) in 18 normal subjects significantly increased urinary citrate and pH (Table 2). As expected, urinary calcium rose. The urinary saturation of calcium oxalate (RSR) rose by only 41% during calcium citrate therapy due mainly to the citrate complexation of calcium (rather than by 62% without such complexation). Moreover, the formation product (FP) of calcium oxalate rose during treatment, indicating that the enhanced citrate excretion augmented the inhibitor activity against calcium oxalate crystallization, probably owing to the rise in urinary citrate (0.63 mmoles).

TABLE 2

EFFECT OF CALCIUM CITRATE ON URINARY BIOCHEMISTRY AND CRYSTALLIZATION

| Urinary | Control Phase | Calcim Citrate |
|---|---|---|
| pH | 5.82 ± .32 | 6.10 ± .33+ |
| Calcium (mg/day) | 150 ± 65 | 248 ± 77+ |
| Citrate (mg/day) | 611 ± 208 | 730 ± 225+ |
| Ammonium (meq/day) | 28.4 ± 5.0 | 22.3 ± 6.2+ |
| Oxalate (mg/day) | 22.3 ± 3.6 | 20.9 ± 4.0 |
| Phosphorus (mg/day) | 538 ± 94 | 451 ± 132+ |
| RSR, Ca Oxalate | 3.16 ± 1.34 | 4.47 ± 1.33+ |
| RSR, Brushite | 0.48 ± 0.39 | 1.02 ± 0.70+ |
| FP, Ca Oxalate ($10^{-8}M^2$) | 3.95 ± 0.59 | 4.38 ± 0.66** |
| FB, Brushite ($10^{-7}M^2$) | 6.36 ± 2.49 | 7.56 ± 2.71 |

Values are resented as mean ± SD. RSR = relative saturation ratio; Fp = formation product; $M^2$ = (moles/liter)$^2$; + = $p < 0.001$; ** = $p < 0.01$.

In a study involving 12 normal subjects, calcium carbonate supplementation (800 mg calcium/day in 4 divided doses) did not alter urinary citrate excretion even though it raised urinary calcium (Table 3). Thus, the urinary saturation of calcium oxalate rose to a greater extent (by 54%) with calcium carbonate than following calcium citrate administration. Moreover, the urinary formation product of calcium oxalate did not change significantly, indicating that the inhibitor activity was unaltered by calcium carbonate.

TABLE 3

EFFECT OF CALCIUM CARBONATE ON URINARY BIOCHEMISTRY AND CRYSTALLIZATION

| Urinary | Control Phase | Calcium Carbonate |
|---|---|---|
| Calcium (mg/day) | 149 ± 60 | 232 ± 73+ |
| Citrate (mg/day) | 640 ± 172 | 694 ± 191 |
| Ammonium (meq/day) | 29.8 ± 4.8 | 23.8 ± 8.4** |
| Oxalate (mg/day) | 22.4 ± 3.79 | 22.7 ± 4.0 |
| Phosphorus (mg/day) | 555 ± 104 | 476 ± 157+ |
| RSR, Ca Oxalate | 3.14 ± 1.53 | 4.85 ± 1.48+ |
| RSR, Brushite | 0.56 ± 0.40 | 1.18 ± 0.74+ |
| FP, Ca Oxalate ($10^{-8}M^2$) | 3.53 ± 0.52 | 3.72 ± 0.42 |

EXAMPLE 7

A Calcium Citrate Dietary Supplement

A typical pharmaceutically acceptable calcium citrate supplement, in capsule or tablet form with about 5 meq calcium (100 mg) contains: calcium citrate (415 mg); pregelatinized starch (24 mg); magnesium stearate (5 mg) and sodium carboxymethylcellulose (6 mg). Many other types of convenient pharmaceutically acceptable calcium citrate supplements are obvious to those skilled in the pharmaceutical arts. This calcium citrate supplement was used to prevent or alleviate osteoporosis.

Changes obvious to those skilled in that art may be made in the various components, steps and procedures described herein without departing from the concept and scope of the invention as defined in the following claims.

What is claimed is:

1. A process for averting the development of osteoporosis or preventing further development of osteoporosis, comprising the steps of:
   identifying individuals susceptible to the development of osteoporosis or already having developed osteoporosis; and
   supplementing the diet of said individuals with a daily amount of calcium citrate comprising between about 0.5 gm calcium and about 2.0 gm calcium.

2. A process for halting the development of further osteoporosis in postmenopausal women comprising the steps of:
   identifying postmenopausal women with developed osteoporosis; and
   administering to said postmenopausal women a daily dietary calcium supplement consisting essentially of calcium citrate and comprising between about 0.5 gm calcium and about 2.0 gm calcium.

3. A process for averting the development of osteoporosis or preventing further development of osteoporosis comprising the steps of:
   identifying individuals susceptible to the development of osteoporosis or already having developed osteoporosis;
   providing a calcium citrate dietary supplement in a pharmaceutically acceptable form; and
   administering to said individuals a daily amount of the calcium citrate dietary supplement, the daily amount comprising between about 0.5 gm calcium and about 2.0 gm calcium.

4. A process for dietary calcium supplementation which allows efficient absorption of calcium from intestines, comprising the steps of:
   providing a pharmaceutically acceptable composition consisting essentially of calcium citrate; and
   supplementing the diet of an individual susceptible to development of osteoporosis with a daily amount of said composition containing from about 0.5 gm to about 2.0 gm calcium, said supplementing inhibiting development of osteoporosis.

5. The process of claim 4 wherein the individual is defined further as being susceptible to calcium nephrolithiasis, and that dietary calcium supplementation reduces the risk of calcium nephrolithiasis.

6. A process for dietary calcium supplementation which allows efficient absorption of calcium from intestines, comprising the steps of:
   providing a pharmaceutically acceptable composition consisting essentially of calcium citrate; and
   supplementing the diet of a postmenopausal woman with a daily amount of said composition containing from about 0.5 gm to about 2.0 gm calcium.

7. A process for dietary calcium supplementation which allows efficient absorption of calcium from intestines, comprising the steps of:
   providing a pharmaceutically acceptable composition consisting essentially of calcium citrate; and
   supplementing the diet of an elderly man with a daily amount of said composition containing from about 0.5 gm to about 2.0 gm calcium.

8. The process of claim 6 or 7 wherein the individual is defined further as being susceptible to calcium nephrolithiasis, the supplementing step is defined further as providing dietary essential calcium, and that dietary calcium supplementation reduces the risk for calcium nephrolithiasis.

9. The process of claim 5, 8, 1 or 2, wherein calcium citrate is in a pharmaceutically acceptable carrier for ease of oral administration.

10. A process for dietary calcium supplementation which allows efficient absorption of calcium from intestines, comprising the steps of:
    providing a pharmaceutically acceptable composition consisting essentially of calcium citrate; and
    supplementing the diet of an individual having a degree of osteoporosis with a daily amount of said composition containing from about 0.5 gm to about 2.0 gm calcium, the supplementing inhibiting further development of osteoporosis.

11. A process for dietary calcium supplementation which allows efficient absorption of calcium from intestines, comprising the steps of:
    providing a pharmaceutically acceptable composition consisting essentially of calcium citrate; and
    supplementing the diet of a postmenopausal woman having a degree of osteoporosis with a daily amount of said composition containing from about 0.5 gm to about 2.0 gm calcium, the supplementing inhibiting further development of osteoporosis.

12. A process for dietary calcium supplementation which allows efficient absorption of calcium from intestines, comprising the steps of:
    providing a composition essentially of calcium citrate and a pharmaceutically acceptable carrier for ease of oral administration; and
    supplementing the diet of an individual having a daily amount of said composition containing from about 0.5 gm to about 2.0 gm calcium.

13. A process for dietary calcium supplementation which allows efficient absorption of calcium from intestines, comprising the steps of:
    providing a pharmaceutically acceptable composition consisting essentially of calcium citrate; and
    supplementing the diet of an individual susceptible to calcium nephrolithiasis and development of osteoporosis with a daily amount of said composition containing from about 0.5 gm to about 2.0 gm calcium dietary calcium supplementation reducing the risk of osteoporosis development with minimal risk of calcium nephrolithiasis.

14. A process for dietary calcium supplementation which allows efficient absorption of calcium from intestines, comprising the steps of:
    providing a pharmaceutically acceptable composition consisting essentially of calcium citrate; and
    supplementing the diet of an individual susceptible to calcium nephrolithiasis with a daily amount of said composition containing from about 0.5 gm to about 2.0 gm calcium, dietary calcium supplementation reducing or eliminating risk of calcium nephrolithiasis.

* * * * *

UNITED STATES PATENT AND TRADEMARK OFFICE
CERTIFICATE OF CORRECTION

PATENT NO. : 4,772,467
DATED : September 20, 1988
INVENTOR(S) : Charles Y. C. Pak, Dallas, Tex.

It is certified that error appears in the above—identified patent and that said Letters Patent is hereby corrected as shown below:

In column 10, line 36, insert the word --consisting-- between the words "composition" and "essentially".

In column 10, line 40, delete the word "from".

In column 10, line 62, insert the word --said-- between the first use of the word "calcium" and the word "dietary".

Signed and Sealed this

Twenty-fifth Day of April, 1989

Attest:

DONALD J. QUIGG

Attesting Officer

Commissioner of Patents and Trademarks